(12) United States Patent
Harichian et al.

(10) Patent No.: US 7,282,471 B2
(45) Date of Patent: Oct. 16, 2007

(54) PERSONAL CARE COMPOSITIONS WITH GLYCERIN AND HYDROXYPROPYL QUATERNARY AMMONIUM SALTS

(75) Inventors: Bijan Harichian, Brookfield, CT (US); Richard Loren McManus, Shelton, CT (US); Megan Kathleen Hurley, Southington, CT (US); Philip Edward Miner, Newtown, CT (US); Prem Chandar, Closter, NJ (US); Stephen Roy Barrow, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 11/222,104

(22) Filed: Sep. 8, 2005

(65) Prior Publication Data

US 2007/0054820 A1   Mar. 8, 2007

(51) Int. Cl.
*C11D 1/62* (2006.01)
*C11D 3/43* (2006.01)

(52) U.S. Cl. .............. 510/130; 510/119; 510/123; 510/432; 510/504

(58) Field of Classification Search ............ 510/119, 510/130, 123, 432, 504
See application file for complete search history.

(56) References Cited

U.S. PATENT DOCUMENTS

| | | | |
|---|---|---|---|
| 4,663,159 A | 5/1987 | Brode, II et al. | |
| 4,689,217 A | 8/1987 | Restaino et al. | |
| 4,690,817 A | 9/1987 | Davis et al. | |
| 4,775,715 A | 10/1988 | Beresniewicz et al. | |
| 4,978,526 A * | 12/1990 | Gesslein et al. | 424/70.28 |
| 5,250,652 A * | 10/1993 | Langer et al. | 528/125 |
| 5,698,183 A | 12/1997 | Langer et al. | |
| 5,773,595 A | 6/1998 | Weuthen et al. | |
| 6,290,978 B2 | 9/2001 | Mak et al. | |
| 6,432,907 B1 | 8/2002 | Skold et al. | |
| 6,620,410 B1 | 9/2003 | Cho et al. | |
| 6,649,177 B2 | 11/2003 | Howard et al. | |
| 6,740,317 B1 | 5/2004 | Cho et al. | |
| 6,869,977 B1 | 3/2005 | O'Lenick, Jr. et al. | |
| 2003/0206933 A1 | 11/2003 | Schulze zur Wiesche et al. | |
| 2003/0211952 A1 | 11/2003 | Erazo-Majewicz et al. | |
| 2004/0156877 A1 | 8/2004 | Tokuyama et al. | |
| 2004/0258654 A1 | 12/2004 | Nielsen et al. | |
| 2006/0088495 A1 * | 4/2006 | Harichian et al. | 424/70.28 |
| 2006/0089277 A1 * | 4/2006 | Harding et al. | 510/123 |

FOREIGN PATENT DOCUMENTS

| | | |
|---|---|---|
| EP | 1366742 | 12/2003 |
| JP | 63068514 | 3/1988 |
| JP | 1249709 | 10/1989 |
| JP | 9012589 | 1/1997 |
| WO | WO90/03161 | 4/1990 |
| WO | 96/35410 | * 11/1996 |
| WO | WO96/35410 | 11/1996 |
| WO | 00/61066 | 10/2000 |
| WO | WO 03/037277 A1 | 5/2003 |

OTHER PUBLICATIONS

Dow—Quat 188 Cationic Monomer: Overview, Jun. 30, 2004.
Arch Personal Care Products Brochure—Honeyquat 50 Substantive Honey Derivative, Jan. 2004.
Arch Personal Care Products—In vivo study of moisturizing effects of HoneyQuat 50, Jan. 2004.
Cola Moist 200 Brochure—2004.
International Search Report, Feb. 6, 2006.

* cited by examiner

*Primary Examiner*—Charles Boyer
(74) *Attorney, Agent, or Firm*—Milton L. Honig

(57) ABSTRACT

A personal care composition is provided formulated with glycerin and a moisturization enhancing agent which is a salt of structure AB, wherein A is a cationic charged component, B is an anionic charged component, and A has at least one quaternized nitrogen atom and at least two hydroxyl groups and a molecular weight no higher than about 400.

7 Claims, No Drawings

US 7,282,471 B2

PERSONAL CARE COMPOSITIONS WITH GLYCERIN AND HYDROXYPROPYL QUATERNARY AMMONIUM SALTS

BACKGROUND OF THE INVENTION

1. Field of the Invention

The invention concerns personal care compositions having excellent moisturization coupled with undiminished skinfeel properties.

2. The Related Art

Dry skin is a problem in varying degree to most humans. This condition is particularly evident in winter. Personal care products such as skin creams/lotions, shampoos/conditioners, toilette bars/shower gels and antiperspirants/deodorants are normally formulated with at least one material to address dry skin. Symptoms such as itching, flaking and a visually displeasing dermal appearance can all to some extent be modulated.

There are three traditional classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

Quaternary ammonium compounds have recently been commercialized as moisturizers. One of these known under the trademark Honeyquat 50 with INCI name of Hydroxypropyltrimonium Honey has been reported to be a better humectant than glycerin at levels of 2%. See the Arch/Brooks brochure titled "Cosmetic Ingredients & Ideas®", Issue No. 2, August 2001. Honeyquat 50 is described as being derived from the reaction of pendent hydroxyl groups (on the disaccharide) of a "light" deodorized grade of honey with a chlorohydroxytrimethylammonium derivative. Another commercial quaternary ammonium moisturizer is Cola™Moist 200 with INCI name of Hydroxypropyl Bis-Hydroxyethyldimonium Chloride. See the Colonial Chemical Inc. brochure titled "Cola™Moist 200", copyright 2004. U.S. Pat. No. 6,869,977 B1 (O'Lenick, Jr. et al.) to Colonial Chemical Inc. discloses a related monocationic material described as a moisturizing agent.

There are several shortcomings in the performance of known humectants. Even the best such as glycerin requires to be formulated at relatively high levels to achieve good moisturization. Very high levels interfere with formulation space, result in poor skinfeel and engender incompatibility with other ingredients.

Accordingly, the present invention seeks to retain the special humectancy of glycerin seen at high concentration levels in a system featuring lower levels that minimize the disadvantages of glycerin.

SUMMARY OF THE INVENTION

A personal care composition is provided which includes:
(i) from about 5 to about 50% by weight of glycerin; and
(ii) from about 0.05% to about 30% by weight of a moisturization enhancing agent which is a salt of structure AB,
wherein A is a cationic charged component of the salt AB,
B is an anionic charged component of the salt AB, and
A has at least one quaternized nitrogen atom, at least two hydroxyl groups and a molecular weight no higher than about 400.

DETAILED DESCRIPTION OF THE INVENTION

Now it has been found that polyhydroxylated quaternary ammonium salts of relatively low molecular weight interact with glycerin to achieve the same robust moisturization formerly only seen with high level glycerin formulas.

Glycerin will be present in amounts ranging from about 5 to about 50%, preferably from about 7 to 40%, more preferably from 10 to about 30%, and optimally from 12 to 20% by weight of the composition.

The moisturization enhancing agent of the present invention is a salt of structure AB, wherein A is a cationic charged component of the salt AB, and B is an anionic charged component of the salt AB, A has at least one quaternized nitrogen atom, at least two hydroxyl groups and a molecular weight no higher than about 400.

Cationic charged component A will have at least one, preferably from one to four, optimally one to two quaternized nitrogen atoms. Further, A will have at least two hydroxyl groups, preferably from two to three hydroxyl groups.

Anionic charged component B may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate. The number and charge of negatively charged component B will be sufficient to neutralize the positive charge of component A.

A preferred embodiment of the moisturization enhancing agent is the dihydroxypropyl tri($C_1$-$C_3$ alkyl)ammonium salts. These salts may be obtained in a variety of synthetic procedures, most particularly by hydrolysis of chlorohydroxypropyltri($C_1$-$C_3$ alkyl)ammonium salts. Ordinarily the $C_1$-$C_3$ alkyl constituent on the quaternized ammonium group will be methyl, ethyl, n-propyl or isopropyl and mixtures thereof. Particularly preferred is a trimethyl ammonium group known through INCI nomenclature as a "trimonium" group. A most preferred species is 1,2-dihydroxypropyltrimonium chloride, wherein the $C_1$-$C_3$ alkyl is a methyl group.

Another preferred embodiment is the dihydroxypropyl di($C_1$-$C_3$ alkyl)mono(hydroxyethyl)ammonium salts. Most preferred is the material of structure (I).

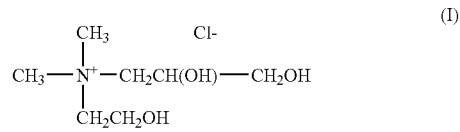

Diquaternary ammonium salts can also be useful in the context of the present invention. A preferred embodiment is Cola™Moist 200 available from the Colonial Chemical Company, Inc., South Pittsburgh, Tenn. This material has the structure (II).

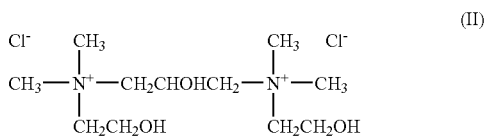

Amounts of the moisturization enhancement agent may range from about 0.05 to about 30%, preferably from about 0.1 to about 25%, more preferably from about 5 to about 20%, optimally from about 10 to about 15% by weight of the composition. Advantageously, weight amounts of glycerin to the agent may be in a ratio of 10:1 to greater than 1:1, preferably from 6:1 to 1.2:1, more preferably from 4:1 to 1.5:1, optimally from 3:1 to 2:1.

By the term personal care composition is meant any substance applied to a human body for improving appearance, cleansing, odor control or general aesthetics. Nonlimiting examples of personal care compositions include leave-on skin lotions and creams, shampoos, hair conditioners, shower gels, toilet bars, antiperspirants, deodorants, dental products, shave creams, depilatories, lipsticks, foundations, mascara, sunless tanners and sunscreen lotions.

Compositions of this invention may also include a cosmetically acceptable carrier. Amounts of the carrier may range from about 1 to 94%, preferably from about 50 to about 90%, optimally from about 65 to about 85% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety.

Emollient materials may serve as cosmetically acceptable carriers. These may be in the form of natural or synthetic esters and hydrocarbons. Amounts of the emollients may range anywhere from about 0.1 to about 60%, preferably between about 1 and about 30% by weight of the composition.

Among the ester emollients are:

(a) Alkyl esters of saturated fatty acids having 10 to 24 carbon atoms. Examples thereof include behenyl neopentanoate, isononyl isononanoate, isopropyl myristate and octyl stearate.

(b) Ether-esters such as fatty acid esters of ethoxylated saturated fatty alcohols.

(c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(d) Wax esters such as beeswax, spermaceti wax and tribehenin wax.

(e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Surfactants may also be present in compositions of the present invention. Total concentration of the surfactant when present may range from about 0.1 to about 50%, preferably from about 1 to about 25%, optimally from about 1 to about 10% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Adjunct humectants may be employed in the present invention. These are generally polyhydric alcohol-type materials. Typical polyhydric alcohols include propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 20%, preferably between 1 and 10%, most preferably between 2 and 8% by weight of the composition.

Sunscreen agents may also be included in compositions of the present invention. Particularly preferred are such materials as ethylhexyl p-methoxycinnamate, available as Parsol MCX®, Avobenzene available as Parsol 1789®, and benzophenone-3 also known as Oxybenzone. Inorganic sunscreen actives may be employed such as microfine (1 to 100 nm) titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminim-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the composition.

Dental products formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases, cellulases, elastases and combinations.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilet bars may have packaging constituted by a cellulosic or plastic wrapper or within a cardboard box or even encompassed by a shrink wrap plastic film.

Another aspect of compositions of this invention may be the inclusion of instructions attached to or otherwise associated with the packaging. The instructions indicate to a consumer topical use of the composition on skin, hair or oral mucosae. Packaging itself will usually be printed with the instructions but sometimes a separate written insert within the package may serve to provide the instructions. Typical language includes phrases such as "apply a thin layer to the underarm", "apply regularly to hands", "apply to wet hair, lather and rinse", "cleanse skin" and "pump a small amount onto the palm of your hand".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Dihydroxypropyltrimonium Chloride | 5.00 |
| PHASE B | |
| Xanthan Gum | 0.20 |
| Natrosol ® 250HHR (ethyl cellulose) | 0.50 |
| Butylene Glycol | 3.00 |
| Glycerin | 10.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

EXAMPLE 2

A water-in-oil topical liquid make-up foundation according to the present invention is described in Table II below.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | balance |
| Dihydroxypropyl Bis-Hydroxyethyldimonium Chloride | 4.00 |
| Methyl Paraben | 0.12 |
| Propylene Glycol | 8.00 |
| Niacinamide | 4.00 |
| Glycerin | 12.00 |
| Sodium Chloride | 2.00 |
| Sodium Dehydroacetate | 0.30 |

EXAMPLE 3

Illustrated herein is a skin cream incorporating glycerin and a quat salt of the present invention.

TABLE III

| INGREDIENT | WEIGHT % |
|---|---|
| Glycerin | 15.00 |
| Niacinamide | 5.00 |
| Dihydroxypropyltrimonium Chloride | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

EXAMPLE 4

Illustrative of another cosmetic composition incorporating glycerin and a quat salt according to the present invention is the formula of Table IV.

TABLE IV

| INGREDIENT | WEIGHT % |
| --- | --- |
| Polysilicone-11 | 29 |
| Cyclomethicone | 59 |
| Glycerin | 10 |
| Dihydroxypropyltrimonium Chloride | 1.2 |
| Dimethicone Copolyol | 0.5 |
| Sunflowerseed Oil | 0.3 |

EXAMPLE 5

A relatively anhydrous composition incorporating glycerin and a quat salt of the present invention is reported in Table V.

TABLE V

| INGREDIENT | WEIGHT % |
| --- | --- |
| Cyclomethicone | 60.65 |
| Glycerin | 15.00 |
| Dimethicone | 10.10 |
| Squalane | 6.00 |
| Dihydroxypropylhydroxyethyldimonium Chloride | 5.00 |
| Isostearic Acid | 1.90 |
| Borage Seed Oil | 0.90 |
| Retinyl Palmitate | 0.25 |
| Ceramide 6 | 0.10 |
| Tocopherol | 0.10 |

EXAMPLE 6

An aerosol packaged foaming cleanser with glycerin and a quat salt suitable for the present invention is outlined in Table VI.

TABLE VI

| INGREDIENT | WEIGHT % |
| --- | --- |
| Sunflower Seed Oil | 10.00 |
| Glycerin | 10.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Hydroxypropyl Bis-Hydroxyethyldimonium Chloride | 1.00 |
| Water | Balance |

EXAMPLE 7

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated 1.0 grams of a composition with glycerin and a quaternary ammonium salt as outlined in Table VII below.

TABLE VII

| INGREDIENT | WEIGHT % |
| --- | --- |
| Dihydroxypropylhydroxyethyldimonium Chloride | 4.00 |
| Glycerin | 12.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance | 0.20 |
| Vitamin E Acetate | 0.001 |
| Water | Balance |

EXAMPLE 8

A toilet bar illustrative of the present invention is outlined under Table VIII.

TABLE VIII

| INGREDIENT | WEIGHT % |
| --- | --- |
| Sodium Soap (85/15 Tallow/Coconut) | 77.77 |
| Dihydroxypropyltrimonium Chloride | 3.50 |
| Glycerin | 8.00 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

EXAMPLE 9

A shampoo composition useful in the context of the present invention is described in Table IX below.

TABLE IX

| Ingredient | Weight % |
| --- | --- |
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Glycerin | 12.00 |
| Hydroxypropyl Bis-Hydroxyethyldimonium Sulfate | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® | 0.0008 |
| Benzyl Alcohol | 0.0225 |
| Water | Balance |

EXAMPLE 10

This Example illustrates an antiperspirant/deodorant formula incorporating the moisturizing actives according to the present invention.

TABLE X

| Ingredient | Weight % |
| --- | --- |
| Cyclopentasiloxane | 39 |
| Dimethicone | 20 |
| Aluminum Zirconium Trichlorohydrex Glycinate | 15 |
| Dihydroxypropyltrimonium Chloride | 5.0 |
| $C_{18}$-$C_{36}$ Acid Triglyceride | 5.0 |
| Microcrystalline Wax | 3.0 |
| Glycerin | 8.0 |
| Silica | 2.5 |
| Dimethicone Crosspolymer | 1.0 |
| Fragrance | 0.5 |
| Disodium EDTA | 0.4 |
| Butylated Hydroxytoluene | 0.3 |
| Citric Acid | 0.3 |

EXAMPLE 11

A toothpaste according to the present invention can be formulated with the ingredients listed under Table XI.

TABLE XI

| Ingredients | Weight % |
| --- | --- |
| Zeodent 115 ® | 20.00 |
| Glycerin | 18.00 |
| Xanthan Gum | 7.00 |
| Sodium Carboxymethyl Cellulose | 0.50 |
| Sodium Bicarbonate | 2.50 |
| Dihydroxypropyltrimonium Chloride | 2.00 |
| Sodium Laurylsulfate | 1.50 |
| Sodium Fluoride | 1.10 |
| Sodium Saccharin | 0.40 |
| Titanium Dioxide | 1.00 |
| Pluronic F-127 ® | 2.00 |
| FD&C Blue No. 1 | 3.30 |
| Menthol | 0.80 |
| Potassium Nitrate | 5.00 |
| Water | balance |

EXAMPLE 12

Moisturization properties of compositions according to the present invention were evaluated in a "SkiCon" Test named for the SkiCon 200 instrument used in performing the analysis. Moisturization is measured on the skin surface through a conductance evaluation (micro Siemens). Depth of measurement is approximately less than 15 μm. The methodology involves use of panelists (usually 10-20 in number). These panelists are requested to pre-wash with a standard Ivory® soap. After 30 minutes, the panelists' skin are measured using the SkiCon 200 instrument. A sample of 0.05 gram experimental product is then applied onto a 5×5 cm area marked on an inner forearm. Post-application measurements are taken two hours after the initial treatment. Results are reported as area measured under a curve graphing % Hydration versus time.

A set of compositions were prepared based on a combination of glycerin and a moisturization enhancing agent (dihydroxypropyltrimonium chloride). Results are recorded under Table XII.

TABLE XII

| SAMPLE CODE | GLYCERIN (%) | DIHYDROXYPROPYL TRIMONIUM CHLORIDE (%) | AREA UNDER THE CURVE |
| --- | --- | --- | --- |
| A | 5 | 0 | 11,400 |
| B | 0 | 3.333 | 8,518 |
| C | 2 | 2 | 8,350 |
| D | 30 | 0 | 33,623 |
| E | 12 | 12 | 45,073 |

Table XII reveals through Sample E relative to D that a high level (30%) of glycerin can be replaced by a lower glycerin amount in combination with a glycerol quat such as dihydroxypropyltrimonium chloride. Equivalent if not better performance is achieved at lower total moisturizer levels.

Attempts to prepare a stabilized system of dihydroxypropyltrimonium chloride in the absence of glycerin resulted in the quat precipitating out. Measurements could not be reliably obtained.

EXAMPLE 13

This Example details the synthesis of 2,3-dihydroxypropyl trimethylammonium chloride (identified in Table XII as dihydroxypropyl trimonium chloride). A 125 ml erlenmeyer flask was charged with 16.7 ml (53 mmol) of 3-chloro-2-hydroxypropyl trimethylammonium chloride (employed as a 60% material in water as Quat 188®). The flask was equipped with a dropping funnel and stirring bar. A solution of sodium hydroxide (55 ml, 55.0 mmol) was charged into the flask via the dropping funnel at a rate to maintain room temperature of the reaction. Once addition was complete, the solution was stirred under ambient conditions for about 12 hours, followed by heating at 50° C. for two hours.

Progress of the reaction was monitored by thin layer chromatography (TLC). Product was spotted on a 2.5 by 7.6 cm silica gel plate alongside the starting material and eluted with butanol:acetic acid:water (4:2:2) for approximately 50 minutes. Visualization was executed with ninhydrin stain and scorching on a hotplate.

Crude product solution was first acidified to pH of 7, and then concentrated to remove water. Ethanol (200 ml) was added to the crude product with stirring. Upon sitting, sodium chloride precipitated and was filtered off under vacuum. The filtrate was concentrated under vacuum on a Rotavap®, followed by additional drying under high vacuum (0.05 mmHg). A cloudy gel was obtained yielding the final product in 97% yield. TLC analysis indicated a major spot at $R_f$=0.27.

A 60 MHz proton NMR ($D_2O$ w/TSP) was run on the final product. The spectra confirmed the final product structure. Mass Spectrum analysis in positive ion mode revealed a $M^+$ of 134 (minus chlorine).

What is claimed is:

1. A personal care composition comprising:
   (i) from 7 to about 50% by weight of glycerin; and
   (ii) from about 0.05% to about 30% by weight of a moisturization enhancing agent which is a dihydroxypropyltri($C_1$-$C_3$ alkyl) ammonium salt having a molecular weight no higher than about 400.

2. The composition according to claim 1 wherein glycerin is present in an amount from 10% to 30% by weight of the composition.

3. The composition according to claim 1 wherein glycerin is present in an amount from 12 to 20% by weight of the composition.

4. The composition according to claim 1 wherein the agent is dihydroxypropyltrimonium chloride.

5. The composition according to claim 1 wherein the glycerin and moisturization enhancing agent are present in a weight ratio ranging from about 6:1 to greater than 1:1.

6. The composition according to claim 1 which is selected from the group consisting of leave-on skin lotions and creams, shampoos, hair conditioners, shower gels, toilette bars, antiperspirants, deodorants, dental products, shave creams, depilatories, lipsticks, foundations, mascara, sunless tanner and sunscreen lotions.

7. The composition according to claim 1 wherein the glycerin and moisturization enhancing agent are present in a weight ratio ranging from 10:1 to greater than 1:1.

* * * * *

UNITED STATES PATENT AND TRADEMARK OFFICE
CERTIFICATE OF CORRECTION

PATENT NO.         : 7,282,471 B2
APPLICATION NO. : 11/222104
DATED              : October 16, 2007
INVENTOR(S)        : Harichian et al.

It is certified that error appears in the above-identified patent and that said Letters Patent is hereby corrected as shown below:

Title page, item (73) Assignee: Should read as follows, --Conopco, Inc., d/b/a Unilever, Englewood Cliffs, NJ--.

Signed and Sealed this

Eighteenth Day of December, 2007

JON W. DUDAS
*Director of the United States Patent and Trademark Office*